(12) United States Patent
Hegedus et al.

(10) Patent No.: US 11,127,504 B2
(45) Date of Patent: Sep. 21, 2021

(54) CUSTOMIZED OPHTHALMIC SURGICAL PROFILES

(71) Applicant: NOVARTIS AG, Basel (CH)

(72) Inventors: Imre Hegedus, Aliso Viejo, CA (US); Hadi Srass, Yorba Linda, CA (US)

(73) Assignee: Alcon Inc.

( * ) Notice: Subject to any disclaimer, the term of this patent is extended or adjusted under 35 U.S.C. 154(b) by 426 days.

(21) Appl. No.: 16/152,313

(22) Filed: Oct. 4, 2018

(65) Prior Publication Data

US 2019/0115108 A1 Apr. 18, 2019

Related U.S. Application Data

(60) Provisional application No. 62/573,209, filed on Oct. 17, 2017.

(51) Int. Cl.
*G16H 50/50* (2018.01)
*A61B 34/10* (2016.01)
(Continued)

(52) U.S. Cl.
CPC ............ *G16H 50/50* (2018.01); *A61B 34/10* (2016.02); *A61F 9/008* (2013.01);
(Continued)

(58) Field of Classification Search
CPC ..... G16H 50/50; A61F 9/00825; A61F 9/008; A61F 2009/0087; A61F 2009/00887; A61F 2009/00872; A61F 2009/00897; A61F 9/00806; A61F 9/00823; A61B 34/10; A61B 2034/104; A61B 90/37; G06F 9/455; A61M 1/00; G02B 26/06; G01M 11/0228
See application file for complete search history.

(56) References Cited

U.S. PATENT DOCUMENTS 6,099,522 A    8/2000  Knopp et al.
6,325,792 B1 * 12/2001  Swinger ............. A61F 9/00804
                                                        606/11
(Continued)

FOREIGN PATENT DOCUMENTS

CN      1744867 A  *  3/2006  ............ A61F 9/008
CN    103892959 A  *  7/2014
(Continued)

OTHER PUBLICATIONS

Gamett et al., "The Ideal Capsulotomy", Cataract & refractive surgery today, , Nov./Dec. 2014.*

*Primary Examiner* — Kandasamy Thangavelu

(57) ABSTRACT

In a general aspect, a customized surgical profile is validated for execution on a surgical system. In some aspects, a customized ophthalmic surgical profile, which includes a surgical pattern and at least one parameter associated with the surgical pattern, is obtained. A pattern definition file executable by a laser-based ophthalmic surgical system is generated based on the customized ophthalmic surgical profile. Execution of the customized ophthalmic surgical profile on the laser-based ophthalmic surgical system is simulated based on the pattern definition file, and the pattern definition file is validated based on an output of the simulation. The validated pattern definition file is provided for execution on the laser-based ophthalmic surgical system.

20 Claims, 4 Drawing Sheets

(51) Int. Cl.
 *A61F 9/008* (2006.01)
 *G06F 9/455* (2018.01)
(52) U.S. Cl.
 CPC ......... *A61F 9/00825* (2013.01); *G06F 9/455* (2013.01); *A61B 2034/104* (2016.02); *A61F 2009/0087* (2013.01); *A61F 2009/00872* (2013.01); *A61F 2009/00887* (2013.01); *A61F 2009/00897* (2013.01)

(56) References Cited

U.S. PATENT DOCUMENTS

| | | | |
|---|---|---|---|
| 9,427,356 | B2 | 8/2016 | Raksi |
| 2004/0059321 | A1 | 3/2004 | Knopp et al. |
| 2010/0076453 | A1* | 3/2010 | Morris .................. G16H 40/40 606/130 |
| 2010/0256964 | A1 | 10/2010 | Rathjen |
| 2010/0256965 | A1 | 10/2010 | Rathjen |
| 2013/0237972 | A1* | 9/2013 | Raksi .................. A61F 9/00825 606/6 |
| 2016/0175145 | A1* | 6/2016 | Raksi .................... G02B 26/06 606/4 |
| 2017/0172803 | A1* | 6/2017 | Chaudhary ......... A61F 9/00825 |
| 2017/0189233 | A1* | 7/2017 | Dewey ............... G01M 11/0228 |

FOREIGN PATENT DOCUMENTS

| | | | | |
|---|---|---|---|---|
| CN | 104093383 | B | * 10/2016 | ............. A61B 90/37 |
| EP | 2236109 | A1 | * 10/2010 | ............. A61F 9/008 |
| EP | 2361068 | A1 | 8/2011 | |
| JP | 2005528600 | A | * 9/2005 | ......... A61F 9/00806 |
| JP | 2012513258 | A | * 6/2012 | ......... A61F 9/00838 |
| JP | 2014524759 | A | * 9/2014 | ......... A61F 9/00825 |
| JP | 2017606573 | A | * 3/2017 | ......... A61F 9/00823 |
| KR | 20120096512 | A | * 8/2012 | ............. A61F 9/008 |
| KR | 20130119417 | A | * 10/2013 | ............. A61F 9/008 |
| KR | 101444757 | B1 | * 9/2014 | |
| WO | WO 9425107 | A1 | * 11/1994 | ............... A61N 5/02 |
| WO | WO 2012135073 | A2 | * 10/2012 | |
| WO | 2015/070092 | A1 | 5/2015 | |
| WO | 2016/061511 | A1 | 4/2016 | |
| WO | WO 2016/148754 | A1 | * 9/2016 | ............. A61M 1/00 |
| WO | WO 2017/003694 | A1 | * 1/2017 | ............. A61F 9/008 |

\* cited by examiner

CUSTOMIZED OPHTHALMIC SURGICAL PROFILES

FIELD

The present disclosure relates to surgical devices, and in particular ophthalmic surgical laser systems.

BACKGROUND

Laser-based surgical systems are used to perform numerous ophthalmic procedures. For example, the LenSx® Laser manufactured by Alcon® is a femtosecond laser system capable of producing precise, image-guided incisions on every plane of the anterior chamber of the eye, including the cornea, capsule, and lens. Other examples include the WaveLight® FS200 and EX500, both of which are manufactured by Alcon®, as well as cataract and refractive surgical lasers manufactured by other companies.

Although many laser-based ophthalmic surgical systems are currently available, there exists a need for with improved versatility, flexibility, customization, and networking capabilities. The present disclosure describes a platform which provides these benefits, and others.

SUMMARY

In certain embodiments, a method includes obtaining a customized ophthalmic surgical profile. The customized ophthalmic surgical profile includes a surgical pattern and at least one parameter associated with the surgical pattern. The method also includes generating, based on the customized ophthalmic surgical profile, a pattern definition file executable by a laser-based ophthalmic surgical system, and simulating, based on the pattern definition file, execution of the customized ophthalmic surgical profile on the laser-based ophthalmic surgical system. The method further includes validating the pattern definition file based on an output of the simulation, and providing the validated pattern definition file for execution on the laser-based ophthalmic surgical system.

In certain embodiments, an ophthalmic surgical computer program is stored on a non-transitory computer-readable medium, and includes a pattern definition engine, a pattern simulation engine, and a pattern validation engine. The pattern definition engine is configured to obtain a customized ophthalmic surgical profile that includes a surgical pattern and at least one parameter associated with the surgical pattern, and generate, based on the customized ophthalmic surgical profile, a pattern definition file executable by a laser-based ophthalmic surgical system. The pattern simulation engine is configured to simulate, based on the pattern definition file, execution of the customized ophthalmic surgical profile on the laser-based ophthalmic surgical system. The pattern validation engine is configured to validate the pattern definition file based on an output of the simulation.

In certain embodiments, a system includes one or more processors and a memory that includes instructions. The instructions are operable, when executed by the one or more processors, to obtain a customized ophthalmic surgical profile that includes a surgical pattern and at least one parameter associated with the surgical pattern, and generate, based on the customized ophthalmic surgical profile, a pattern definition file executable by a laser-based ophthalmic surgical system. The instructions are also operable to simulate, based on the pattern definition file, execution of the customized ophthalmic surgical profile on the laser-based ophthalmic surgical system, validate the pattern definition file based on an output of the simulation, and provide the validated pattern definition file for execution on the laser-based ophthalmic surgical system.

Certain embodiments may provide one or more technical advantages, in some instances. For example, surgical patterns and parameters for a laser-based ophthalmic surgical system may be modified or otherwise customized. In some instances, operators of the system (e.g., surgeons) can modify previously-created surgical patterns and parameters, such as, for example, to customize a surgical pattern to a particular patient's eye. The custom surgical patterns and parameters may be validated, such as by a third party (e.g., the manufacturer of the surgical system), to ensure the patterns and parameters may be safely and properly executed by a target surgical system. In some instances, validated surgical patterns and parameters may be stored in a repository and shared with other surgical system operators. By allowing development of custom patterns and parameters by third parties, development cycles for the patterns and parameters may be shortened.

These and other advantages will be apparent to those skilled in the art in view of the present drawings and specification.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

Figure 1:
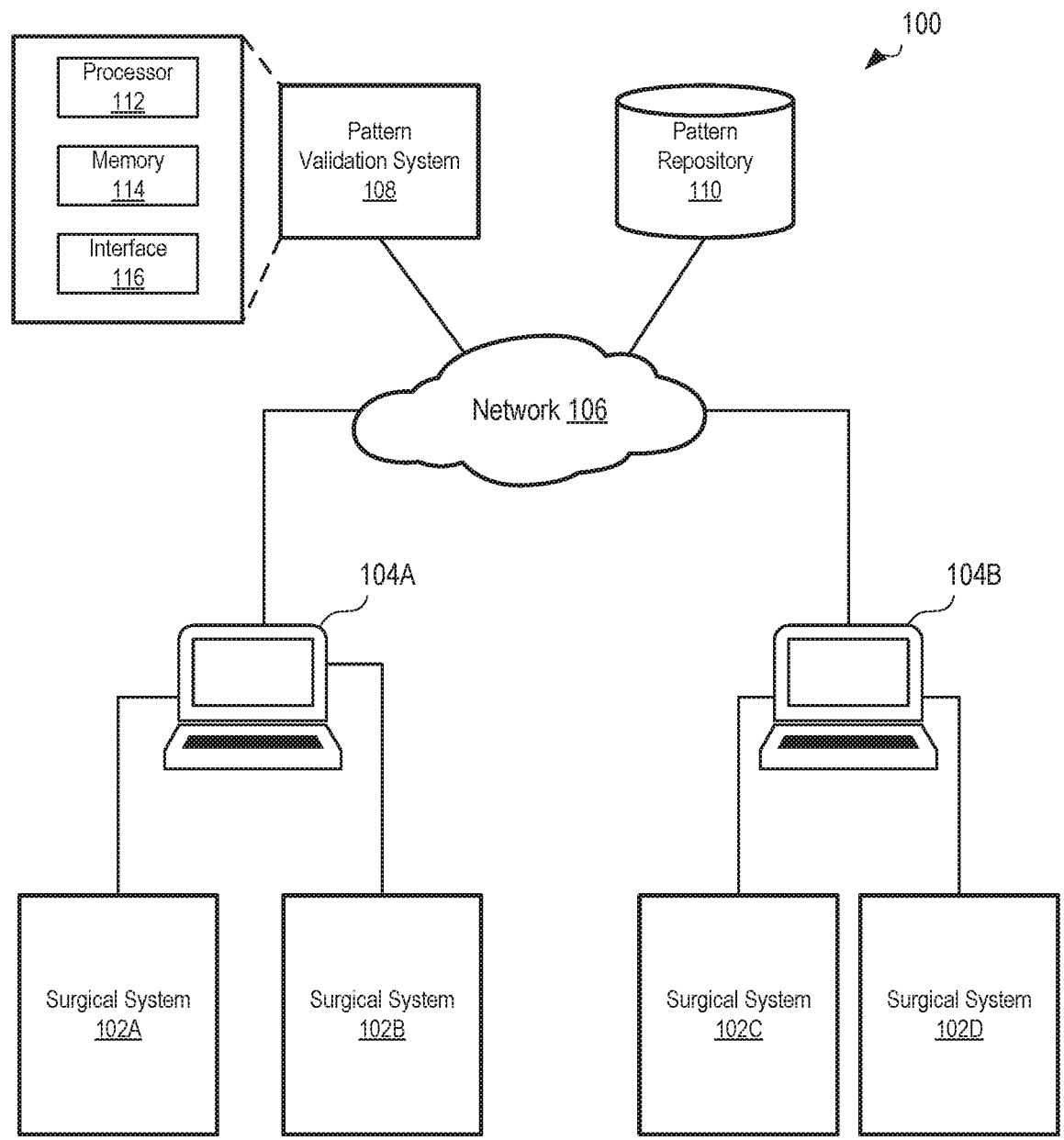
FIG. 1 illustrates a block diagram of an example surgical system.

One skilled in the art will understand that the drawings, described below, are for illustration purposes only, and are not intended to limit the scope of applicant's disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Alterations and further modifications to the described systems, devices, and methods, and any further application of the principles of the present disclosure are contemplated as would normally occur to one skilled in the art to which the disclosure relates. In particular, it is contemplated that the systems, devices, and/or methods described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

FIG. 1 is a block diagram of an example surgical profile validation system 100. The example system 100 comprises multiple target surgical systems 102 that are communicatively coupled to pattern design systems 104. The target surgical systems 102 and the pattern design systems 104 are also communicatively coupled to a pattern validation system 108 and a pattern repository 110 through the network 106. The network 106 may include via any suitable combination of wired and/or wireless networks (e.g., Ethernet, optical fiber, IEEE 802.11, cellular, Internet, etc.). In some instances, the target systems 102 and the pattern design systems 104 may be managed by a clinic, and may be co-located or distributed in different geographic locations. For instance, in the example shown, the target systems 102A, 102B and the pattern design system 104A may be associated with a first clinic, and the target systems 102C, 102D and the pattern design system 104B may be associated with a second clinic. The system 100 may include additional pattern design systems 104 and target systems 102 communicatively coupled to the pattern validation system 108 and the pattern repository 110, that are associated with one or more clinics.

The target surgical systems 102 may include any suitable surgical system. For example, in some instances, each of the target surgical systems 102 is a laser-based ophthalmic surgical system that is suitable for performing refractive, cataract, vitro retinal, or other ophthalmic surgical procedures. The laser-based ophthalmic surgical system may include a laser system (e.g., a femtosecond, picosecond, or excimer laser system) along with other optical components (e.g., lenses, mirrors, or diffraction gratings) that direct pulses from the laser to pre-determined locations within a patient's eye. For example, in some embodiments, the target surgical systems 102 includes a laser system configured to generate a pulsed laser beam, scanning optical elements configured to scan the pulsed laser beam in three dimensions, and a laser controller configured to execute a pattern definition file to control the laser system and the scanning optical elements according to a customized surgical profile defined by the pattern definition file. As an example, each of the target systems 102 may be a LenSx® system or a WaveLight® FS200 or EX500 system.

The pattern design systems 104 may include any suitable system for designing or customizing a surgical profile for execution on a target surgical system 102. A customized surgical profile may comprise a set of scan patterns, incisions, shapes, and laser energy parameters, pulse duration parameters, repetition rate parameters, and the like, which collectively define and control how a surgical laser and associated components perform a specific laser surgical procedure. A customized surgical profile may be embodied in a pattern definition file, as described herein. For example, the pattern design systems 104 may be computer systems (e.g., a server, PC, laptop, tablet, or other computer or mobile device) that run an operating system (e.g., Windows, Linux, macOS, iOS, Android, etc.) and execute stored computer programs that allow a user to design a customized surgical profile (which may be embodied as a file or data stored on non-transitory computer readable medium) by, for example, selecting or modifying one or more surgical patterns, shapes, or parameters related to a surgical procedure to be performed on a target surgical system 102. The computer programs may include one or more software modules or engines encoded with logic to provide various functionalities related to designing a customized surgical profile. For example, the computer program may include one or more of the software engines described below with respect to the pattern design system 210 of FIG. 2.

The pattern validation system 108 may include any suitable system for validating a customized surgical profile created using a pattern design system 104. For example, the pattern validation system 108 may be a computer system (e.g., a server, PC, laptop, tablet, or other computer or mobile device) that runs an operating system (e.g., Windows, Linux, macOS, iOS, Android, etc.) and executes stored computer programs that simulate execution of the customized surgical profile, validate the safety and efficacy pattern based on the simulation, and provide a validated pattern definition file for execution on a target surgical system 102. The computer programs may include one or more software modules or engines that provide various functionalities related to the validation of a customized surgical profile created by a pattern design system 104. For example, the computer program may include one or more of the software engines described below with respect to the pattern design system 210 of FIG. 2. In some instances, the pattern validation system 108 may also include a licensing module operable to verify licenses, permissions, or other information associated with the pattern design systems 104 during the validation (e.g., to ensure the pattern design system 104 is authorized to customize surgical profiles and submit the profiles for validation). For example, in response to an operator selecting a particular pattern definition file for execution on a target system 102, target system 102 or pattern design system 104 may send a validation and license verification request that includes an identifier or credentials for the target system or the operator and a pattern definition file identifier to pattern validation system 108. A validation module of validation system 108 may execute a process to validate that the selected pattern definition file is safe and effective for use by the target system 102. For instance, the validation request may, in some examples, include patient-specific information (e.g., eye biometry data, OCT image data, risk factor data, etc.), and the validation module may run a validation process to confirm that the selected pattern definition file is safe and effective for use by the target system 102 based on patient-specific information. Additionally, the licensing module of validation system 108 may authenticate (e.g., by comparing information in the validation and license verification request with information in a database storing operator license data) the requesting operator or target system, for example, by determining whether the operator or target system is currently licensed or otherwise has permission to execute the selected pattern definition file. If the validation request and license check are both confirmed, the licensing module may send a confirmation to target system 102, allowing it to proceed with the selected pattern definition file. If the validation request or license check is not confirmed, the licensing module may send a denial to target system 102. In some embodiments, the denial may include an explanation of why the validation request or license check was not confirmed, and may initiate a process by which the operator of target system 102 may modify the pattern definition file to pass the validation check or obtain a license (e.g., by submitting a single-use, multi-use, or subscription license fee. Accordingly, in some implementations, the customized surgical profile may not be executable on a target surgical system 102 (e.g., on an actual patient) until the pattern validation system 108 has validated the pattern definition file and confirmed that the user has a license to use it.

Surgical profiles that have been validated by the pattern validation system 108 may be stored in the pattern repository 110. Target surgical systems 102 can access and execute validated surgical profiles stored in the pattern repository 110. In some instances, for example, a surgical profile may initially be designed by the pattern design system 104A for execution on the target surgical system 102A. After the pattern has been validated, the target surgical system 102A may access the pattern from the pattern repository 110 and execute the pattern on a patient. The target surgical system 102A may access and execute the same pattern stored in the pattern repository 110 on another patient. Similarly, the target surgical systems 102B, 102C, 102D may access and execute the same pattern stored in the pattern repository 110 on another patient. In some implementations, pattern validation system 108 may re-validate a pattern definition file for individuals based on patient-specific data before allowing the pattern to be executed by a surgical system 102.

In the example shown, the pattern validation system 108 includes a processor 112, a memory 114, and an interface 116. The example processor 112 executes instructions, for example, to generate output data based on data inputs. The instructions can include programs, codes, scripts, or other types of data stored in memory. Additionally or alternatively, the instructions can be encoded as pre-programmed or re-programmable logic circuits, logic gates, or other types of hardware or firmware components. The processor 112 may be or include a general purpose microprocessor, as well as a specialized co-processor or another type of data processing apparatus. In some cases, the processor 112 performs high level operation of the pattern validation system 108. For example, the processor 112 may be configured to execute or interpret software, scripts, programs, functions, executables, or other instructions stored in the memory 114 to simulate execution of a customized pattern definition file and validate the pattern definition file based on the simulation (e.g., as described below in the process 400 of FIG. 4). In some instances, the processor 112 includes multiple processors.

The example memory 114 includes computer-readable media, for example, a volatile memory device, a non-volatile memory device, or both. The memory 114 can include one or more read-only memory devices, random-access memory devices, buffer memory devices, or a combination of these and other types of memory devices. The memory 114 may store instructions that are executable by the processor 112. For example, the instructions may include instructions for simulating execution of a customized pattern definition file and validating the pattern definition file based on the simulation (e.g., as described below in the process 400 of FIG. 4).

The example interface 116 provides communication between the pattern validation system 108 and one or more other devices. For example, the interface 116 may include a network interface (e.g., a wireless interface or a wired interface) operable to communication with one or more of the pattern design systems 104 over the network 106. The interface 116 may also include interfaces allowing interaction with the pattern validation system 108 by a user, such as a keyboard, mouse, touchscreen, and the like.

The example system 100 may include additional, fewer, or different components from those shown in FIG. 1, in certain embodiments. For example, the system 100 can include different types of target surgical systems 102 (e.g., different types or models of laser-based ophthalmic surgical systems). Additionally, components of the system 100 may be portions of the same system, in certain embodiments. For example, the pattern validation system 108 and the pattern repository 110 may comprise logical portions of the same computer system.

Figure 2:
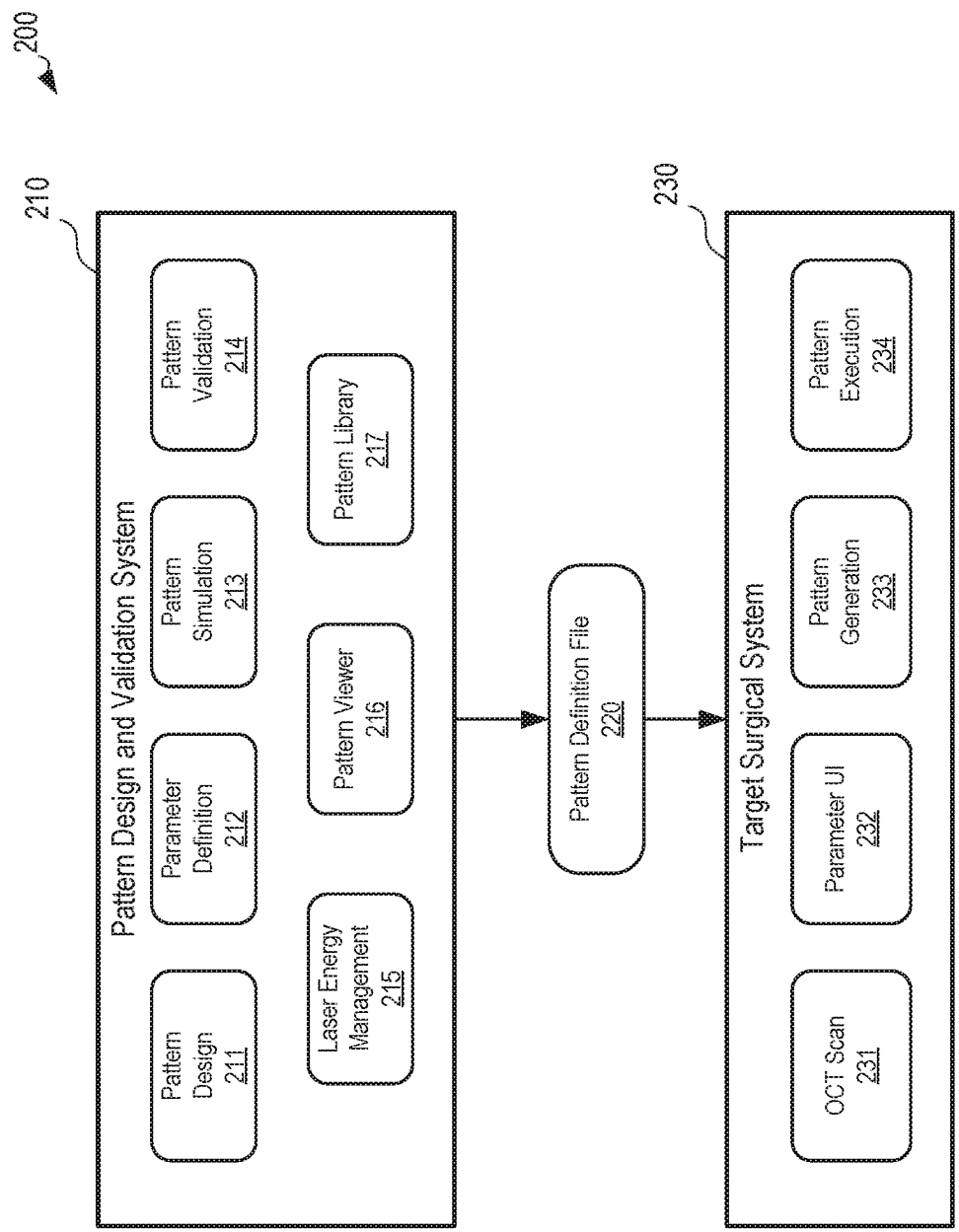
FIG. 2 is a block diagram of an example surgical profile design system.

FIG. 2 is a block diagram illustrating the architecture of an example surgical profile design system 200. The example surgical profile design system includes software engines that make up an ophthalmic surgical computer program designed for execution by one or more computers running an operating system. The example surgical profile design system 200 includes a pattern design and validation system 210 and a target surgical system 230. In certain embodiments, the pattern design and validation system 210 generates and validates a pattern definition file 220 that is provided for execution on the target surgical system 230. The pattern definition file 220 may be system-agnostic, in that it may be executed on one or more different types or models of target surgical systems 230. The pattern design and validation system 210 may generate and validate the pattern definition using one or more software engines. For instance, in the example shown, the pattern design and validation system 210 includes a pattern design engine 211, a parameter definition engine 212, a pattern simulation engine 213, a pattern validation engine 214, a laser energy management engine 215, a pattern viewer engine 216, and a pattern library 217. The target surgical system 230 includes an optical coherence tomography (OCT) scan engine 231, a parameter user interface 232, a pattern generation engine 233, and a pattern execution engine 234.

The example pattern design engine 211 performs one or more operations related to the design and configuration of a customized surgical profile. The pattern design engine 211 may allow the operator to create a customized surgical profile from a blank template, or modify one or more aspects of a surgical pattern stored in the pattern library 217 to produce a customized surgical profile. For example, the pattern library 217 may include pre-defined surgical patterns (e.g., two- or three-dimensional patterns similar to those shown in FIGS. 3A-3B) that the pattern design engine 211 may access and provide to an operator for use as a template. In some instances, pattern design engine 211 may allow an operator to duplicate patterns, combine one or more patterns, modify (e.g., remove, rotate, tilt, scale, or otherwise modify) one or more incision lines, geometric shapes, or freeform shapes within a pattern, or create new patterns from a blank template. The pattern design engine 211 may allow the operator to define aspects of the customized surgical profile, such as surgical volume limitations, entry incision locations, incision profile characteristics, scanning pattern characteristics (e.g., spiral, circle, raster, etc.), or a sequence for the various incision lines in the pattern.

The example parameter definition engine 212 performs one or more operations related to defining the parameters associated with the customized surgical profile designed with the pattern design engine 211. For example, in some embodiments, the parameter definition engine 212 may receive data from the pattern design engine 211, laser energy management engine 215, or a system operator via a user interface, and use the information to generate recommended or mandatory parameters such as laser repetition rate and pulse energy in the pattern definition file 220. Example parameters defined or generated by parameter definition engine 212 include a laser pulse repetition rate, laser pulse energy profile, laser pulse spot size, laser pulse duration, laser scan speed, and laser scan pattern (e.g., raster, spiral, etc.). Such parameters may be uniform or vary in different areas or stages of a customized surgical profile. The information generated by the parameter definition engine 212 may include one or more parameters relating to the execution of the customized surgical profile on a target surgical system 230. For example, the parameter definition engine 212 may receive or access information identifying capabilities or limitations of a particular target surgical system 230 or components thereof (e.g., the laser engine, laser delivery system, laser scanner, OCT imaging system, microscope, visualization system, or subcomponents such as motors, actuators, lenses, optical elements, etc.) and, based on such information, generate parameters for components of the target surgical system during execution of the customized surgical profile. In some examples, the parameter definition engine 212 may override user-selected parameters based on known system limitations or capabilities. The parameters generated may be used to control and operate the various components of the target surgical system 230 during execution of the customized surgical profile. In some instances, the parameter definition engine 212 can also receive data from the laser energy management engine 215 that is used to generate one or more parameters used to generate the pattern definition file 220.

The example laser energy management engine 215 performs one or more operations related to defining operation of the laser (or other components) in the target surgical system 230. For example, the laser energy management engine 215 may generate recommended or mandatory laser energy, spot size, or repetition rate parameters at various points along incision lines in the pattern based on information received from the pattern design engine 211, parameter definition engine 212, or known capabilities and limitations of the target surgical system 230. In some implementations, parameters generated by the parameter definition engine 212 are included in the pattern definition file 220 generated by the pattern design and validation system 210.

The example pattern simulation engine 213 performs one or more operations related to virtual execution of the parameters generated by the parameter definition engine 212. For example, the pattern simulation engine 213 may generate a series of scan points associated with the incision lines of the surgical pattern along with laser pulse energy levels for each of the respective points, modeling how the target surgical system 230 would execute the parameters of the pattern definition file 220. In some embodiments, for instance, the pattern simulation engine 213 calculates a plurality of x-y-z scan coordinates that correspond to the specified incision lines and parameters generated by the parameter definition engine 212 based on the customized surgical profile, and determines a pulse energy for each of the x-y-z scan coordinates. In some embodiments, the parameter simulation engine 212 also simulates execution of the surgical pattern at a fixed or variable laser pulse repetition rate specified in the parameters generated by the pattern definition engine 212. In some embodiments, the pattern simulation engine 213 also defines a layering pattern for the x-y-z scan coordinates. The example pattern validation engine 214 performs one or more operations related to validating the data in the pattern definition file 220. In some embodiments, the pattern validation engine 214 receives data generated by the pattern simulation engine 213, and analyzes the data to determine whether the pattern may be executed properly or safely by the target surgical system 230. For example, the pattern validation engine 214 may analyze distances between the x-y-z scan coordinates generated by the pattern execution and determine whether the target surgical system 230 can operate and scan its laser in such a way to safely and accurately generate pulses at each of the x-y-z scan coordinates. Such a determination may take into account known capabilities and limitations of aspects of target surgical system, such as laser scanner galvanometer speed and reach, maximum laser repetition rate, or whether the laser repetition rate is variable and, if so, how quickly. As another example, the pattern validation engine 214 may analyze the energy levels at various x-y-z scan coordinates or across a total customized surgical pattern to determine the energy levels that may be generated by the laser system of the target surgical system 230 and evaluate whether the energy levels are safe for use in a surgical procedure performed on a patient. In some implementations, validation engine 214 may override operator-selected design elements or parameters (e.g., shapes, volume, repetition rate, repetition variability, energy profile) to render the customized pattern safe and effective for use by the target surgical system 230. In some examples, validation engine 214 may present the operator with suggestions for how to modify design elements or parameters to make the customized pattern safe and effective. Validation engine 214 may provide notifications or messages via the user interface to communicate the operations and results of the validation process.

The example pattern viewer engine 216 performs one or more operations related to visualizing the customized surgical profile. For example, the pattern viewer engine 216 may, during the design phase, generate a visualization of the surgical pattern of the customized surgical profile as the pattern is modified by an operator. In some embodiments, the visualization may be a two-dimensional visualization with different views of the customized surgical profile (e.g., similar to the patterns 300 shown in FIGS. 3A-3B, or may be a three-dimensional rendering of the customized surgical profile. The two-dimensional or three-dimensional visualizations may, in some implementations, be manipulated by a user by, for example, rotation, zooming in or out, layering, drilling down, etc. In certain implementations, pattern viewer engine 216 may generate a visualization of the pulse energy and total energy associated with the surgical scan pattern of the customized surgical profile. For example, pattern viewer engine 216 may generate an energy map (e.g., heat map of energy associated with regions of the surgical profile) illustrating the pulse energy at different locations in the surgical pattern. In certain implementations, pattern viewer engine 216 may generate a visualization representing laser engine or scanner characteristics, such galvanometer position. One or more such visualizations may be presented to an operator using a display, tablet, projector, 3D visualization system, or the like communicatively coupled to pattern design and validation system 210.

Pattern design engine 211, parameter definition engine 212, pattern simulation engine 213, pattern validation engine 214, laser energy management engine 215, pattern viewer engine 216, and pattern library engine 217 may together provide an intuitive user interface (output to a display, tablet, projector, 3D visualization system, or the like) for the operator to build, view, and modify the customized surgical profile. For instance, the pattern design engine 211 and pattern viewer engine 216 may, together or independently, provide a two- or three-dimensional visualization of the pattern (e.g., similar to the diagrams shown in FIGS. 3A-3B) to an operator during the customization process using display, tablet, projector, 3D visualization system, or the like. The user interface may allow the operator to position, scale, tilt, rotate or otherwise modify a view of the customized pattern, as well as definable aspects of the customized pattern such as incision position, shape, and size (as discussed above with respect to pattern design engine 211). Additionally, parameter definition engine 212 and pattern viewer engine 216 may, together or independently, provide within the user interface selectable elements (e.g., icons, menus, text entry, etc.) which allow the operator to choose parameter values associated with the customized pattern (as discussed above with respect to parameter definition engine 212). Accordingly, multiple components of pattern design and validation system 210 may interact to provide a user interface for building, modifying, and viewing a customized scan pattern.

Turning to target surgical system 230, the example OCT scan engine 231 performs one or more operations related to performing an OCT scan on a patient's eye. The OCT scan can control an OCT imaging system which uses interferometry to image surfaces and tissues on or in the eye, and generate a visualization of structures within the patient's actual eye. In some embodiments, the OCT scan engine 231 may receive information (e.g., instructions) from the pattern definition file 220 that indicates how the OCT scan should be performed and controls scanning and operation of an OCT imaging system integrated with our coupled to target surgical system 230

The example parameter user interface 232 performs one or more operations related to visualizing one or more aspects of the customized surgical profile defined by the pattern definition file 220. For example, the parameter user interface 232 may generate and cause display of a visualization of the surgical pattern and parameters contained in the pattern definition file 220. In some embodiments, the parameter user interface 232 generates and displays a two- or three-dimensional visualization of what the customized surgical profile may look like when executed. In some implementations, the visualization may be combined, juxtaposed, or overlaid on an image or video feed generated by the OCT imaging system, a surgical microscope, a 3D visualization system, or the like. For example, data from a microscope and OCT imaging system of the target surgical system 230 may be combined with a generated visualization of the surgical pattern by parameter user interface 232 to generate (e.g., to a surgeon) a visualization of the customized surgical profile as applied to the patient's actual eye. The parameter user interface 232 may allow an operator (e.g., a surgeon) to make one or more modifications to the customized surgical profile using input commands received from a keyboard, mouse, touchscreen, and the like, in certain embodiments. The modifications may be made based on one or more modification limits contained in the pattern definition file 220.

The example pattern generation engine 233 performs one or more operations related to generating executable instructions for the target surgical system 230 based on the pattern definition file 220. In some embodiments, for instance, the pattern generation engine 233 calculates a plurality of x-y-z scan coordinates that correspond to incisions and parameters specified in the pattern definition file 220, and determines a pulse energy for each of the x-y-z scan coordinates. In some embodiments, the pattern generation engine 233 can optimize one or more parameters in the pattern definition file based on one or more characteristics of the target surgical system 230 (e.g., based on the model of the target surgical system 230). For example, the pattern generation engine 233 may optimize a velocity or acceleration, or a repetition rate of one or more surgical control elements (e.g., the laser engine, scanning optical elements of the laser delivery system, or other components of the target surgical system 230) based on the capabilities of the particular target surgical system 230 selected to execute the pattern definition file 220. For example, if a target surgical system is capable of laser pulse repetition rate changes "on the fly", then a laser pulse repetition rate may be optimized for various segments in the surgical pattern (e.g., based on depth of the incision). Similarly, if a target surgical system is capable of laser pulse energy changes "on the fly", then a pulse-specific laser pulse energy may be optimized for various segments in the surgical pattern (e.g., based on depth of the incision). In addition, the pattern generation engine 233 may optimize a scan pattern to account for the physical characteristics and limitations of a particular laser scanner associated with target surgical system 230. For example, the pattern generation engine 233 may generate a specific scan pattern (e.g., spiral, raster, etc.) or layer pattern for the y-z scan coordinates, which may be tailored to the capabilities and limitations of the laser scanner to be utilized. In some instances, such optimization may minimize a total procedure time, such as, for example, by increasing the laser pulse repetition rate for portions of the scan pattern or accounting for the capabilities of the laser scanning elements (e.g., the surgical reach of galvanometer mirrors and the like). In some instances, such optimization may limit or reduce the total energy being applied to the patient's eye. In some embodiments, optimization may improve laser spot precision and accuracy or reduce mechanical strain on the laser scanning elements.

The example pattern execution engine 234 performs one or more operations related to executing the customized surgical profile on the target surgical system. For example, the pattern execution engine 234 may execute the instructions generated by the pattern generation engine 233. The pattern execution engine 234 may control one or more surgical control elements of the target surgical system. For example, the pattern execution engine may control firing of the laser engine, movement of the scanning optical elements (e.g., mirrors, focusing lenses, etc.) in the laser scanner (which scan the laser pulse through the x-y-z scan coordinates), or other components of the target surgical system 230.

The example system 200 may include additional, fewer, or different components from those shown in FIG. 2, in certain embodiments. For example, the pattern design and validation system 210 or the target surgical system 230 may each include additional software engines or modules than those shown. Additionally, components of the system 200 may be portions of separate systems, in certain embodiments. For example, certain engines shown in the pattern design and validation system may be stored or executed on different computer systems (e.g., some engines stored and executed on a pattern design system and others stored and executed on a pattern validation system).

Figure 3B:
FIGS. 3A-3B are diagrams showing example ophthalmic surgical patterns.
Figure 3A:
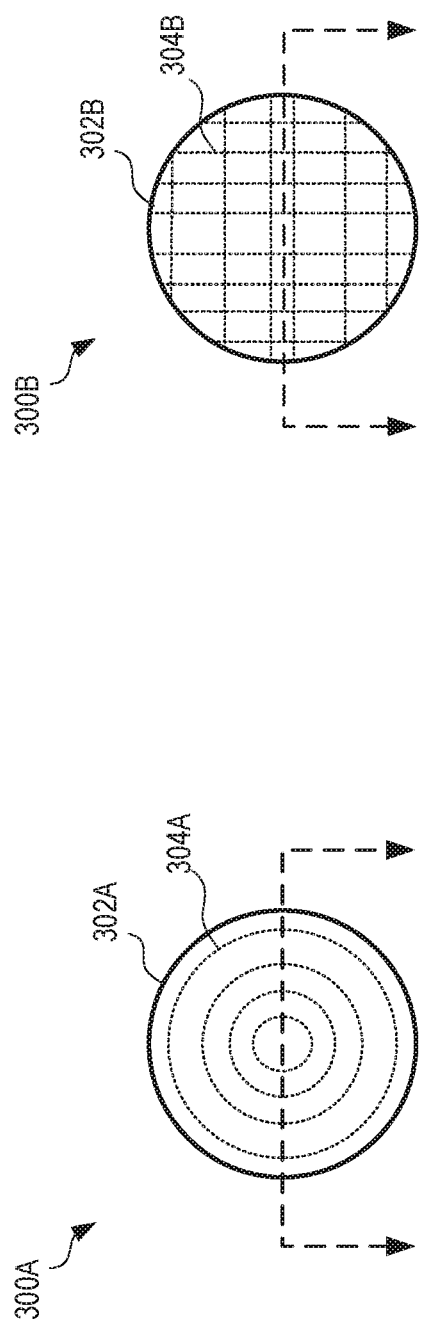

FIGS. 3A-3B are diagrams showing example ophthalmic surgical patterns 300. In the example shown, the patterns 300 are lens fragmentation patterns. In some implementations, however, the ophthalmic surgical patterns may include corneal incision patterns, capsulotomy incision patterns, ablation patterns, entry incisions, or other types of ophthalmic laser surgical patterns. The diagrams shown in FIGS. 3A-3B include a top view and side view of incision lines 304, 306 the respective patterns overlaid on a lens 302. In certain embodiments, the example ophthalmic surgical patterns 300 may be executed on a lens of a patient's eye by a laser-based ophthalmic surgical system. In some embodiments, the patterns 300 may include one or more parameters associated with the incision lines 304 (e.g., a laser pulse energy at one or more points along the incision lines, a laser pulse repetition rate at various segments of the incision lines, or both). The pattern and parameters may be displayed by a graphical user interface to an operator that is customizing the pattern or about to execute the pattern on a target surgical system. In the example shown in FIG. 3A, the top view shows a pattern of concentric incision lines 304 that are centered on the lens 302, and the side view shows a pattern of incision lines 306 at different depths within the lens 302. In the example shown in FIG. 3B, the top view shows a pattern of rectangular-shaped incision lines 304 along the lens 302, and the side view shows a pattern of incision lines 306 at different depths within the lens 302.

In some embodiments, an operator of a pattern design system (e.g., the pattern design systems 104 of FIG. 1) may define and modify one or more aspects of the patterns shown in FIGS. 3A-3B. For example, referring to the system 100 of FIG. 1, the patterns 300 may be stored in the pattern repository 110 or locally at a pattern design system 104. The pattern design system 104 being used by an operator may access the patterns 300 and display the patterns and associated parameters to the operator via a user interface. In some embodiments, the user interface may display the patterns 300 as shown in FIGS. 3A-3B. The patterns 300 may be displayed to the operator in another manner as well (e.g., a text-based interface, 3D visualization, etc.). Through the pattern design system 104, the operator may define or modify one or more aspects of the patterns 300. For example, the operator may move certain incision lines 304, 306 in the pattern 300, remove certain of the incision lines 304, 306 from the pattern 300, or add additional incision lines 304, 306 to the pattern 300. The operator may manipulate incisions lines 304, 306 or create new incision lines to define customized geometric or freeform shapes, volumes, or patterns. As another example, the operator may modify one or more energy levels for the incision lines 304, 306, such as to increase a laser pulse energy level at different depths within the lens 302 (to account for increased attenuation of the laser pulse as it moves through the lens toward a deeper depth). As another example, a laser pulse repetition rate may be modified (e.g., slowed or accelerated) at one or more segments within the surgical pattern. Other aspects of the patterns 300 may be modified as well. After the pattern 300 has been customized, it may be validated as described below with respect to process 400 of FIG. 4.

Figure 4:
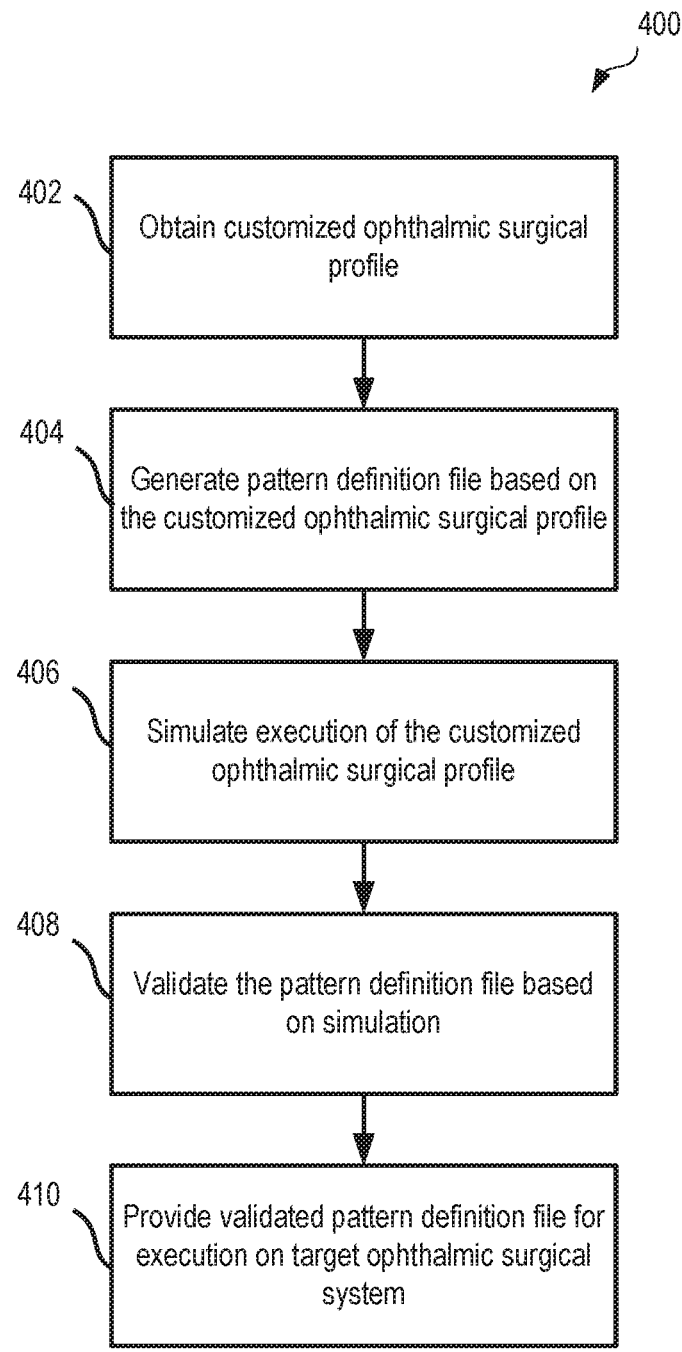
FIG. 4 is a flow diagram showing an example process of validating a customized ophthalmic surgical profile.

FIG. 4 is a flow diagram showing an example process 400 of validating a customized ophthalmic surgical profile. Operations in the example process 400 may be performed by a data processing apparatus (e.g., the processor 112 of the example pattern validation system 108 of FIG. 1). Operations in the example process 400 may be performed by one or more multiple computer devices. For instance, one or more operations of the process 400 may be performed by a pattern design computer system (e.g., implemented similar to the pattern design systems 104 of FIG. 1), and other operations of the process 400 may be performed by a pattern validation computer system (e.g., implemented similar to the pattern validation system 108 of FIG. 1). The example process 400 may include additional or different operations, and the operations may be performed in the order shown or in another order. In some cases, one or more of the operations shown in FIG. 4 are implemented as processes that include multiple operations, sub-processes, or other types of routines. In some cases, operations can be combined, performed in another order, performed in parallel, iterated, or otherwise repeated or performed another manner.

At 402, a customized ophthalmic surgical profile is obtained. The customized ophthalmic surgical profile may include an ophthalmic surgical pattern and one or more parameters associated with the ophthalmic surgical pattern. The ophthalmic surgical pattern may include a lens fragmentation pattern, a corneal incision pattern, a capsulotomy incision pattern, another type of ophthalmic surgical pattern, or a combination thereof. The parameters associated with the ophthalmic surgical pattern can include, for example, laser energy levels at various incision points within an eye (e.g., within a lens), geometric or freeform shapes defining incision lines, a distance between incision lines in the ophthalmic surgical pattern (e.g., radii of concentric circle incision lines as shown in FIG. 3A, or dimensions of cuboid shapes formed by the fragmentation pattern as shown in FIG. 3B), laser pulse repetition rates (overall or at different segments of the surgical pattern), or other parameters (e.g., parameters associated with operation of the target surgical system executing the customized surgical profile). For instance, referring to the system 100 of FIG. 1, the pattern validation system 108 may obtain a customized ophthalmic surgical profile intended to be executed on one or more of the target surgical systems 102. The customized ophthalmic surgical profile may be generated by a pattern design system 104 using a computer program implemented thereon. For example, referring to the system 200 of FIG. 2, the customized ophthalmic surgical profile may be generated using one or more of the engines in the pattern design and validation tool 210, as described above. The customized ophthalmic surgical profile may include a validation and license verification request that requests verification of execution of the customized ophthalmic surgical profile and authentication of an operator providing the customized ophthalmic surgical profile, as described further below.

At 404, a pattern definition file is generated. The pattern definition file may be generated in a format that is executable by a laser-based ophthalmic surgical system or a computer or server supporting a pattern design and validation system 210. The pattern definition file may be generated by any suitable system based on the customized ophthalmic surgical profile obtained at 402. For example, referring to the system 100 of FIG. 1, either a pattern design system 104 or the pattern validation system 108 may generate the pattern definition file based on a customized ophthalmic surgical profile developed by one of the pattern design systems 104. In some embodiments, the pattern definition file may be agnostic as to the type or model of the target surgical system. For example, the pattern definition file may be formatted in such a way that it may be directly or indirectly executed on multiple different models of ophthalmic surgical systems. In some examples, the pattern definition file may be compiled into an executable file for execution by different models of ophthalmic surgical systems.

At 406, execution of the customized ophthalmic surgical profile obtained at 402 is simulated. The simulation may be based on the pattern definition file generated at 404. In some embodiments, the simulation models one or more surgical control elements in the laser-based ophthalmic surgical system during execution of the customized ophthalmic surgical profile. In some embodiments, simulating the customized ophthalmic surgical profile includes calculating laser scan coordinates for the customized surgical pattern, laser pulse energy parameters for each of the scan coordinates, galvanometer positioning for each of the scan coordinates and sequences, and a procedure time. For example, a plurality of x-y-z scan coordinates that correspond to the parameters in the pattern definition file may be generated based on the ophthalmic surgical pattern in the customized surgical profile, pulse energies for each of the x-y-z scan coordinates may be determined based on the parameters in the customized surgical profile. In some embodiments, a layering pattern for the x-y-z scan coordinates may also be determined. The x-y-z scan coordinates may be executed by a simulation engine that simulates operation of the target laser-based ophthalmic surgical system. In some instances, the simulation engine may be implemented similar to the pattern simulation engine 213 of FIG. 2. In some embodiments, simulating execution of the customized ophthalmic surgical profile includes optimizing laser pulse parameters (e.g., pulse frequency, duration, energy), scanning patterns, and galvanometer mirror positioning for the laser scan coordinates based on a characteristic of the laser-based ophthalmic surgical system. For example, a duration or energy of laser pulses called for by the customized surgical profile may be modified based on the capabilities of the target laser-based ophthalmic surgical system on which the profile will be executed. As another example, laser pulse repetition rates and scan patterns may be modified based on the capabilities of the target laser-based ophthalmic surgical system. Other aspects of the execution may be simulated as well, such as an overall time that the surgical pattern will take to execute on the target surgical system.

At 408, the pattern definition file is validated based on the simulation at 406. The validation process may include verification of each aspect of the simulated execution of the customized surgical profile. In some embodiments, for instance, validation includes calculating a surgical volume, local and total energy, and procedure time of the simulated application of the customized surgical laser pattern, and determining whether the surgical volume, total energy, and procedure time comply with predetermined thresholds for the target surgical system. For example, the validation process may verify that a surgical volume dictated by the pattern definition file does not exceed predetermined volume parameters, that a laser energy level does not exceed a predetermined total energy or damage threshold, that a laser energy level is appropriate for the surgical procedure (e.g., safe and effective for the intended procedure), or that a laser pulse repetition rate and scan pattern does not exceed limits of the target surgical system (imposed, e.g., by the surgical reach of galvanometer mirrors in the laser scanner). In some embodiments, validating the pattern definition file includes modifying the pattern definition file to allow the file to be executed on the laser-based ophthalmic surgical system. For example, the pattern definition file as generated prior to validation may not be in a format that is executable by a target surgical system. If the validation succeeds, then the pattern definition file may be modified such that is may be executable by a target surgical system. In some implementations, validation may be performed by a software engine that analyzes the simulated operation of the target laser-based ophthalmic surgical system based on the pattern definition file. In some instances, the validation engine may be implemented similar to the pattern validation engine 214 of FIG. 2.

In some embodiments, the validation process also includes an authentication process. The authentication process may include a credential verification, license verification, or other type of verification that ensures the target surgical system or operator thereof has permission (e.g., from a manufacturer of the target surgical system or software provider for the target surgical system) to execute the pattern definition file. For example, the customized ophthalmic surgical profile may include a license verification request that includes credentials for an operator of the target surgical system (e.g., a username/password combination) or license credentials (e.g., identifying a type of license the operator owns), and the authentication process may compare the credentials with information in a database (e.g., operator license data) to determine whether the operator is authorized to execute the pattern definition file on target system. If the operator is not authorized, a message may be generated to the operator. The message may include an explanation of why the operator was not authorized. The message may also initiate a process by which the operator of the target surgical system can obtain a license (e.g., by submitting a single-use, multi-use, or subscription license fee).

At 410, a validated pattern definition file is provided for execution on a target ophthalmic surgical system. For example, referring to the example system 100 of FIG. 1, the pattern validation system 108 may provide a validated version of a pattern definition file directly to a target surgical system 102, or to a pattern design system 104 that loads the pattern definition file on the target surgical system 102 for execution. In some embodiments, if the pattern definition file is not validated at 408, an error message or other notification may be sent. For example, referring to the system 100 of FIG. 1, the pattern validation system 108 may generate and send a message indicating the validation failure to the pattern design system 104 that uploaded the pattern definition file for validation. In some embodiments, after validation at 410, the pattern definition file may be stored in a pattern repository. For example, referring to the example system 100 of FIG. 1, the pattern validation system 108 may validate a pattern definition file, provide the validated pattern definition file to one or more of the pattern design systems 104 or target surgical systems 102, and then store the validated pattern definition file in the pattern repository 110 so that the pattern may be accessed at a later time (e.g., for further modification, or for another execution by another target surgical system).

Some of the subject matter and operations described in this specification can be implemented in digital electronic circuitry, or in computer software, firmware, or hardware, including the structures disclosed in this specification and their structural equivalents, or in combinations of one or more of them. Some of the subject matter described in this specification can be implemented as one or more computer programs, i.e., one or more modules of computer program instructions, encoded on a computer-readable storage medium for execution by, or to control the operation of, data-processing apparatus. A computer-readable storage medium can be, or can be included in, a computer-readable storage device, a computer-readable storage substrate, a random or serial access memory array or device, or a combination of one or more of them. Moreover, while a computer-readable storage medium is not a propagated signal, a computer-readable storage medium can be a source or destination of computer program instructions encoded in an artificially generated propagated signal. The computer-readable storage medium can also be, or be included in, one or more separate physical components or media (e.g., multiple CDs, disks, or other storage devices).

Some of the operations described in this specification can be implemented as operations performed by a data processing apparatus on data stored on one or more computer-readable storage devices or received from other sources. The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them.

A computer system may include a single computing device, or multiple computers that operate in proximity or generally remote from each other and typically interact through a communication network. Examples of communication networks include a local area network ("LAN") and a wide area network ("WAN"), an inter-network (e.g., the Internet), a network comprising a satellite link, and peer-to-peer networks (e.g., ad hoc peer-to-peer networks). The computer system may include one or more data processing apparatuses coupled to computer-readable media storing one or more computer programs that may be executed by the one or more data processing apparatuses, and one or more interfaces for communicating with other computer systems.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program, or in multiple coordinated files (e.g., files that store one or more modules, sub programs, or portions of code). A computer program can be deployed to be executed on one computer or on multiple computers that are located at one site or distributed across multiple sites and interconnected by a communication network.

Embodiments of the present disclosure provide methods and systems for creating, validating, and re-using customized surgical profiles which may overcome limitations of conventional systems and methods. It will be appreciated that above-disclosed and other features and functions, or alternatives thereof, may be desirably combined into many other different systems or applications in accordance with the disclosure. It will also be appreciated that various presently unforeseen or unanticipated alternatives, modifications, variations, or improvements therein may be subsequently made by those skilled in the art which alternatives, variations and improvements are also intended to be encompassed by the following claims.

What is claimed is:

1. A method of validating a customized ophthalmic surgical profile, comprising:
    obtaining a customized ophthalmic surgical profile, the customized ophthalmic surgical profile comprising an surgical pattern and at least one parameter associated with the surgical pattern;
    generating, based on the customized ophthalmic surgical profile, a pattern definition file executable by a laser-based ophthalmic surgical system;
    simulating, based on the pattern definition file, execution of the customized ophthalmic surgical profile on the laser-based ophthalmic surgical system;
    validating the pattern definition file based on an output of the simulation, wherein validating the pattern definition file further comprises calculating a total energy of the simulated application of the customized surgical laser profile and determining whether the total energy comply with a predetermined threshold; and
    providing the validated pattern definition file for execution on the laser-based ophthalmic surgical system.

2. The method of claim 1, wherein generating the pattern definition file comprises generating a plurality of parameters for components of the laser-based ophthalmic surgical system based on the surgical pattern and the at least one parameter.

3. The method of claim 1, wherein simulating execution of the customized surgical profile comprises:
    calculating laser scan coordinates for the customized laser surgical profile; and
    determining a laser pulse energy for each of the scan coordinates.

4. The method of claim 3, wherein simulating execution of the customized surgical profile further comprises optimizing at least one laser pulse parameter for the laser scan coordinates based on a characteristic of the laser-based ophthalmic surgical system.

5. The method of claim 1, wherein simulating execution of the customized ophthalmic surgical profile comprises simulating at least one surgical control element of the laser-based ophthalmic surgical system during execution of the customized ophthalmic surgical profile.

6. The method of claim 1, wherein validating the pattern definition file comprises:
    calculating a surgical volume and procedure time of the simulated application of the customized surgical laser profile; and
    determining whether the surgical volume and procedure time comply with predetermined thresholds.

7. The method of claim 1, wherein the customized ophthalmic surgical profile comprises a validation and license verification request, and validating the pattern definition file comprises verifying execution of the pattern definition file on the laser-based ophthalmic surgical system, authenticating an operator of the laser-based ophthalmic surgical system, and modifying the pattern definition file to allow the file to be executed on the laser-based ophthalmic surgical system.

8. The method of claim 1, wherein the surgical pattern includes a lens fragmentation pattern, a corneal incision pattern, or a capsulotomy incision pattern, and the at least one parameter includes laser energy levels for incision lines of the surgical pattern or a laser pulse repetition rate.

9. The method of claim 1, wherein obtaining the customized ophthalmic surgical profile comprises receiving the customized ophthalmic surgical profile at a first computer system remotely located from the laser-based ophthalmic surgical system, and providing the validated pattern definition file for execution on the laser-based ophthalmic surgical system comprises sending the validated pattern definition file from the first computer system to a second computer system communicably coupled to the laser-based ophthalmic surgical system.

10. A non-transitory computer-readable medium storing an ophthalmic surgical computer program, comprising:
    a pattern definition engine configured to:
        obtain a customized ophthalmic surgical profile, the customized ophthalmic surgical profile comprising a surgical pattern and at least one parameter associated with the surgical pattern;
        generate, based on the customized ophthalmic surgical profile, a pattern definition file executable by a laser-based ophthalmic surgical system;
    a pattern simulation engine configured to simulate, based on the pattern definition file, execution of the customized ophthalmic surgical profile on the laser-based ophthalmic surgical system; and a pattern validation engine configured to validate the pattern definition file based on an output of the simulation, wherein validating the pattern definition file further comprises calculating a total energy of the simulated application of the customized surgical laser profile and determining whether the total energy comply with a predetermined threshold.

11. The non-transitory computer-readable medium storing an ophthalmic surgical program of claim 10, wherein the pattern simulation engine is configured to:
calculate laser scan coordinates for the surgical pattern; and
determine a laser pulse energy for each of the scan coordinates.

12. The non-transitory computer-readable medium storing an ophthalmic surgical program of claim 10, wherein the pattern simulation engine is configured to optimize at least one laser pulse parameter for the laser scan coordinates based on a characteristic of the laser-based ophthalmic surgical system.

13. The non-transitory computer-readable medium storing an ophthalmic surgical program of claim 10, wherein the pattern simulation engine is configured to simulate at least one surgical control element of the laser-based ophthalmic surgical system during execution of the customized ophthalmic surgical profile.

14. The non-transitory computer-readable medium storing an ophthalmic surgical program of claim 10, wherein the pattern validation engine is configured to:
calculate a surgical volume, total energy, and procedure time of the simulated application of the customized surgical laser pattern; and
determine whether the surgical volume, total energy, and procedure time comply with predetermined thresholds.

15. A system, comprising:
one or more processors; and
a memory comprising instructions that are operable, when executed by the one or more processors, to:
obtain a customized ophthalmic surgical profile, the customized ophthalmic surgical profile comprising a surgical pattern and at least one parameter associated with the surgical pattern;
generate, based on the customized ophthalmic surgical profile, a pattern definition file executable by a laser-based ophthalmic surgical system;
simulate, based on the pattern definition file, execution of the customized ophthalmic surgical profile on the laser-based ophthalmic surgical system;
validate the pattern definition file based on an output of the simulation; and
provide the validated pattern definition file for execution on the laser-based ophthalmic surgical system, wherein validating the pattern definition file further comprises calculating a total energy of the simulated application of the customized surgical laser profile and determining whether the total energy comply with a predetermined threshold.

16. The system of claim 15, wherein the instructions for generating the pattern definition file are operable to generate a plurality of parameters for components of the laser-based ophthalmic surgical system based on the surgical pattern and the at least one parameter.

17. The system of claim 15, wherein the instructions for simulating execution of the customized ophthalmic surgical profile are operable to:
calculate laser scan coordinates for the customized laser surgical pattern; and
determine a laser pulse energy for each of the scan coordinates.

18. The system of claim 15, wherein the instructions for simulating execution of the customized ophthalmic surgical profile are operable to simulate at least one surgical control element of the laser-based ophthalmic surgical system during execution of the customized ophthalmic surgical profile.

19. The system of claim 15, wherein the instructions for validating the pattern definition file are operable to:
calculate a surgical volume, total energy, and procedure time of the simulated application of the customized surgical laser pattern; and
determine whether the surgical volume, total energy, and procedure time comply with predetermined thresholds.

20. The system of claim 15, wherein the instructions for validating the pattern definition file are operable to verify execution of the pattern definition file on the laser-based ophthalmic surgical system and modify the pattern definition file to allow the file to be executed on the laser-based ophthalmic surgical system.

* * * * *